United States Patent
Ballinger, Jr. et al.

(10) Patent No.: US 10,400,138 B2
(45) Date of Patent: Sep. 3, 2019

(54) EXTENDED PERFORMANCE BIRD REPELLENT EXTERIOR COATING

(71) Applicant: Arkion Life Sciences, New Castle, DE (US)

(72) Inventors: Kenneth E. Ballinger, Jr., Kennett Square, PA (US); Thomas A. Jerrell, Manchester, NH (US)

(73) Assignee: Arkion Life Sciences, LLC, New Castle, DE (US)

( * ) Notice: Subject to any disclaimer, the term of this patent is extended or adjusted under 35 U.S.C. 154(b) by 0 days.

(21) Appl. No.: 15/629,262

(22) Filed: Jun. 21, 2017

(65) Prior Publication Data

US 2017/0367327 A1   Dec. 28, 2017

Related U.S. Application Data

(60) Provisional application No. 62/353,770, filed on Jun. 23, 2016.

(51) Int. Cl.
| | | |
|---|---|---|
| *A01N 35/06* | (2006.01) |
| *C09D 201/00* | (2006.01) |
| *C09D 5/00* | (2006.01) |
| *C09D 7/63* | (2018.01) |
| *C08K 5/08* | (2006.01) |
| *C08K 5/01* | (2006.01) |
| *C08K 5/07* | (2006.01) |
| *C08K 5/18* | (2006.01) |
| *C08K 5/372* | (2006.01) |

(52) U.S. Cl.
CPC .......... *C09D 201/00* (2013.01); *A01N 35/06* (2013.01); *C09D 5/00* (2013.01); *C09D 7/63* (2018.01); *C08K 5/01* (2013.01); *C08K 5/07* (2013.01); *C08K 5/08* (2013.01); *C08K 5/18* (2013.01); *C08K 5/372* (2013.01)

(58) Field of Classification Search
None
See application file for complete search history.

(56) References Cited

U.S. PATENT DOCUMENTS

| | | |
|---|---|---|
| 5,885,604 A | 3/1999 | Ballinger, Jr. |
| 5,922,774 A | 7/1999 | Winslow |
| 5,990,219 A * | 11/1999 | Sakai ............... C09D 5/36 106/417 |
| 6,324,986 B1 | 12/2001 | Rossmann et al. |
| 6,328,986 B1 | 12/2001 | Ballinger, Jr. |
| 7,488,493 B2 | 2/2009 | Ballinger, Jr. et al. |
| 2015/0208657 A1 | 7/2015 | Ballinger, Jr. |
| 2016/0157477 A1 | 6/2016 | Ballinger, Jr. et al. |

* cited by examiner

*Primary Examiner* — Brian Gulledge
(74) *Attorney, Agent, or Firm* — McCarter & English, LLP

(57) ABSTRACT

The invention relates to the use of a persistent, weatherable blend of a bird repellent and a paint coating composition on exterior surfaces such as wood or building materials, to deter birds from damaging such wood or building material. The bird repellent blend has improved weatherability while retaining the effectiveness of the bird repellent.

12 Claims, 9 Drawing Sheets
(9 of 9 Drawing Sheet(s) Filed in Color)

EXTENDED PERFORMANCE BIRD REPELLENT EXTERIOR COATING

CROSS-REFERENCE TO RELATED APPLICATIONS

This application claims the benefit of 35 U.S.C. § 119 based on the priority of U.S. Provisional Patent Application No. 62/353,770 filed Jun. 23, 2016, which is hereby incorporated by reference.

FIELD OF THE INVENTION

The invention is directed to a bird repellent coating for deterring birds from damaging a variety of exterior surfaces. More particularly, the invention relates to a blend of a bird repellent such as anthraquinone and a paint coating composition.

BACKGROUND OF THE INVENTION

The co-existence of humans and wild birds has always been an important relationship for both species. For humans, this relationship has been a pleasant one esthetically and a useful one ecologically. In the former case, the sights and sounds of birds are universally enjoyed by people of all ages. In the latter case, the role of birds in the ecological chain vis-à-vis birds, carrion and other species is essential. It is, of course, essential that both relationships be preserved.

Notwithstanding the beneficial and pleasant aspects of the interface between wild birds and humans, the propensity of birds to alight on, occupy and damage solid surfaces associated with or near human activity frequently becomes a source of conflict.

Damage to wood-containing substrates, and even some non-wood-containing substrates, from birds, pests and fungus can be serious. For example, woodpeckers are notorious for their strong pointed beak that is used to penetrate wood in search of insects and hollow out wood for nesting. Woodpeckers often cause damage to building exteriors in search of food or shelter. Holes can be drilled into wood siding, eaves, window frames and trim boards. Other nesting birds, such as house wrens, tree swallows, barn swallows, pigeons, mourning doves, can either attach a nest to the side of buildings or hollow out space to support nests. In addition to the direct damage to the substrates, the nesting materials and remains of the bird feces (very acidic) can cause collateral damage to the building materials.

Building materials, both wood containing (or cellulosic based) and non wood containing, are susceptible for damage caused by birds. For example, various bird species have recently adapted to man-made building materials as a preferred substitute for their natural habitat. Acorn woodpecker (*Melanerpes formiciverous*) have begun to use recycled plastic components formed into architectural trim and artificial stucco for a variety of purposes. The birds can cause significant damage to a home.

Similarly, pileated woodpeckers (*Dryocopus pileatus*) have been using western power poles as nest boxes. The pileated woodpecker is a crow sized woodpecker with a very strong bill. With their size and power, they are able to carve very large holes in utility poles. These holes cause significant structural damage and weaken the pole. Downy woodpeckers (*Picoides pubescens*) and hairy woodpeckers (*Picoides villosus*) are known to attack cedar siding of homes and cedar shake siding. These birds use the siding for nests and to make loud noises for mating in the spring.

Surface treatment of food sources and perching areas using bird repellents is known. U.S. Pat. No. 6,324,986 is directed to a method for deterring birds from perching on plant and structural surfaces. U.S. Pat. No. 7,488,493 is directed to a performance aid composition to improve the effectiveness of 9,10-anthraquinone as a pest control. U.S. Ser. No. 14/607,561 is directed to deterrence of birds using a quinone compound present beneath the surface of a material and unavailable for visual inspection or transfer.

A recurring problem, however, is that exterior application of bird repellents becomes susceptible to weathering and loses its effect in short periods of time. As such, there is a need in the industry for a bird repellent vehicle that is capable of remaining adhered to exterior surfaces, such as wood and other solid surfaces, for extended periods of time, withstanding extreme weather conditions (i.e. weatherability), while also retaining the effectiveness of the bird repellent.

SUMMARY OF THE INVENTION

In its primary aspect, the invention is directed to a bird repellent coating blend comprising a bird repellent composition and a paint coating composition.

The invention is also directed to an exterior substrate comprising a bird repellent coating blend wherein the bird repellent blend comprises a bird repellent composition and a paint coating composition.

The invention is further directed to a method of applying a bird repellent composition to an exterior substrate, the method comprising:
 preparing a bird repellent blend comprising at least one bird repellent composition and a paint coating composition;
 adhering said bird repellent blend to said exterior substrate;
 whereby said bird repellent composition remains adhered to said exterior substrate for a period of time longer than when said bird repellent composition is applied to said substrate without being blended with the paint coating composition; and whereby the bird repellent composition remains bioavailable during the period of time that the bird repellent blend is adhered to the exterior surface.

BRIEF DESCRIPTION OF THE DRAWING

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
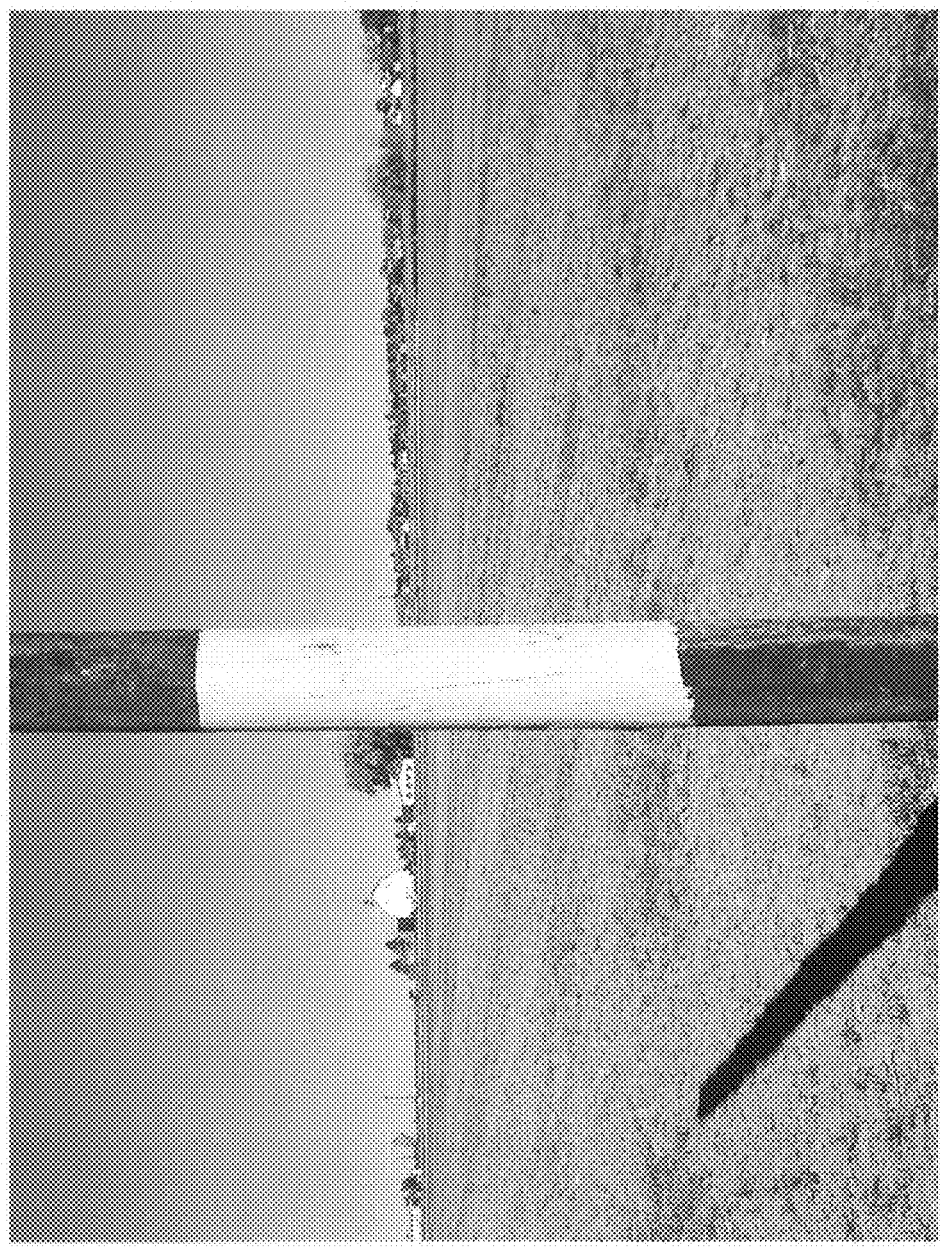
FIG. 1 is a photographic image of a pole treated with anthraquinone on the day of application.

The present disclosure relates to the use of various bird repellent compositions to protect exterior substrate surfaces, such as wood and other building materials from bird damage. In particular, the disclosure relates to the use of a persistent, weatherable blend of a bird repellent composition and a paint coating composition on exterior surfaces such as wood or building materials, to deter birds from damaging such exterior substrates.

The present disclosure relates to a blend of a bird repellent composition and a paint coating composition whereby when the bird repellent composition is blended with the paint coating composition, the resulting bird repellent blend has improved weatherability while retaining the effectiveness (or bioavailability) of the bird repellent composition itself. Such a result was previously not thought possible because the typical bird repellent composition releases onto the bird upon contact. In other words, repellency typically takes effect upon casual contact by the birds whereby the repellent adheres to bird feet and feathers when the birds land on the treated surface, and thusly enters their digestive system as a consequence of preening behavior. However, when blended with a paint coating composition, the bird repellent is no longer available to the birds upon causal contact, and as such, would not be expected to have a repellency effect, or otherwise be bioavailable. It is our finding, however, that even when blended with a paint coating composition, the bird repellent retains its effectiveness.

In one embodiment, the present disclosure relates to a method of reducing or preventing damage to an exterior substrate, such as a wood-containing substrate, the method including applying to a surface of the substrate a blend of at least one bird repellent composition and at least one paint coating composition. In a further embodiment, the present disclosure relates to a method for applying a bird repellent composition to an exterior substrate, the method comprising, preparing a bird repellent blend comprising at least one bird repellent composition and a paint coating composition; adhering said bird repellent blend to said exterior substrate; whereby said bird repellent blend remains adhered to said exterior substrate for a period of time longer than when said bird repellent composition is applied to said substrate without being blended with the paint coating composition; and whereby the bird repellent composition maintains its effectiveness as a bird repellent during the period of time that the bird repellent blend is adhered to the exterior surface.

In some embodiments, the present disclosure is effective to reduce or prevent damage to exterior substrates, such as wood containing substrates, caused by birds, such as woodpeckers. In some embodiments, the damage to an exterior substrate may be reduced by about 100%, or about 95%, or about 90%, or about 80%, or about 70% or about 60%, or about 50% or about 40%, or about 30%. In other embodiments, the reduction or prevention in damage may be effective for up to about 3 months after treatment, or about 6 months after treatment, or about 9 months after treatment, or about 1 year after treatment, or about 2 years after treatment or about 5 years after treatment. The measure of the damage reduction or prevention can be made by many means. For example, the reduction of damage may be measured by the increased working life of the substrate or the amount of time, effort or materials to repair the substrate.

The exterior substrate of the present disclosure can be any substrate used for exterior purpose. For example, the exterior substrate can be wood (creosote or non-creosite treated), power poles, telephone poles, outdoor lumber, dimensional lumber, pressure treated lumber, shingles, siding (e.g., cedar siding), decks, porches, plastics, architectural foam, stucco, artificial wood products, or other similar building materials.

It is important to the effectiveness of the invention that the bird repellent, in whatever physical form it is applied, be persistent. That is, the applied active bird repellent composition must be able to resist erosion by wind and rain and other environmental forces to which the treated surface is exposed. For this reason, it is preferred (1) that the active form of the bird repellent have a relatively low solubility in water so that it is not easily washed off the treated surfaces, and (2) that it have a relatively high melting temperature so that it does not undergo excessive evaporation or sublimation from the treated surfaces during exposure to high ambient temperatures. For these reasons, it is preferred that the active bird repellent material has a solubility in pure water under ambient temperature conditions of no more than about 1000 ppm and preferably at least 0.01-200 ppm, and even more preferably 80-100 ppm. It is further preferred that the melting temperature of the active bird repellent component is at least about 100° C. or above, and more preferably at least about 200° C. or above, or at least about 250° C. or above. A preferred bird repellent is anthraquinone, which has a melting temperature of about 286° C.

Even when the active bird repellent material possesses the above-described preferred physical properties, the material may have poor persistence because it does not adhere well to the surface to which it is applied. The present disclosure is thus directed to a formulation that enables the bird repellent material to adhere to an exterior substrate surface with substantially improved persistence as compared to previous applications of the same bird repellent. As described herein, persistence of the bird repellent on exterior surfaces is substantially improved because the bird repellent is combined with a paint coating composition prior to application. Therefore, even though highly water-insoluble bird repellent compounds are preferred, less insoluble compounds are nevertheless usable in the invention due to the presence of the paint coating composition.

The bird repellent blend of the present disclosure is preferably a blend of at least one bird repellent composition and at least one paint coating composition. In one embodiment of the invention, the bird repellent material is blended with a paint coating composition capable of adhering the bird repellent in a bioavailable state on an exterior substrate surface over a period of 1, 5, 10, 15, 20, 25, 30, 35, 40, 45, 50, 55, 60, 65, 70, 75, 80, 85 or 90 days; or 1, 2, 3, 4, 5, 6, 7, 8, 9, or 10 weeks; or 1, 2.3, 4, 5, 6, 7, 8, 9, 10, 11 or 12 months; or 1, 2, 3, 4, or 5 years. These values can also be used to define a range, such as about 30 days to about 90 days. In some embodiments, the range can be 3 months to 12 months. In other embodiments, the range can be 2 years to 5 years.

What is also beneficial about the bird repellent blend of the present disclosure, is that once applied to an exterior substrate surface, the bird repellent material itself remains bioavailable to the birds and as such, effective as a repellent. When combined with the paint coating composition, the bird repellent no longer casually comes off on the birds as it would normally do without the coating. Instead, while not being tied to any particular theory as to the mechanism of action of the bird repellent blend, it is thought that when the bird pecks the coated surface, in turn breaking the film barrier, the bird becomes exposed to the bird repellent material by direct oral contact, thus ultimately leading to repellency.

Preferred paint coating compositions include paint and primer coatings that are exterior grade and have the capability to remain secured to a substrate surface over long periods of time and are generally resistant to extreme weather conditions. Some examples include acrylic polymers, primers and paints, acrylic/latex primers and paints, alkyd-based primers and paints, hydrophobic polymers, water-based acrylic emulsion primers and paints, acrylic sealing primers and paints, styrene acrylic primer and paint, and polyurethane latex primers and paints just to name a few.

The amount of bird repellent composition in the bird repellent blend of the present disclosure can vary depending upon the type of bird repellent and/or paint coating composition being used in the blend. The bird repellent blend can contain about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 wt % of the bird repellent composition. These values can also be used to define a range, such as about 0.3 wt % to about 0.6 wt %. In some embodiments, the bird repellent blend contains about 0.5 wt % to about 5 wt %, or about 1 wt % to about 3 wt % bird repellent composition. In other embodiments, the bird repellent blend contains about 10 wt % to about 50 wt % bird repellent composition, or about 10 wt % to about 30 wt % bird repellent composition, or about 40 wt % to about 60 wt % bird repellent composition. In even other embodiments, the bird repellent blend contains about 25 wt % bird repellent composition or about 50 wt % bird repellent composition.

The volume ratio of bird repellent composition to the paint coating composition can range from about 10:1 to about 1:10. In some embodiments, the ratio can be 10:2, 10:3, 10:4, 10:5, 10:6, 10:7, 10:8, 10:9, 9:1, 9:2, 9:3, 9:4, 9:5, 9:6, 9:7, 9:8, 9:9, 9:10, 8:1, 8:2, 8:3, 8:4, 8:5, 8:6, 8:7, 8:8, 8:9, 8:10, 7:1, 7:2; 7:3, 7:4, 7:5, 7:6, 7:7, 7:8, 7:9, 7:10, 6:1, 6:2, 6:3, 6:4, 6:5, 6:6, 6:7, 6:8, 6:7, 6:10, 5:1, 5:2, 5:3, 5:4, 5:5, 5:6, 5:7, 5:8, 5:9, 5:10, 4:1, 4:2, 4:3, 4:4, 4:5, 4:6, 4:7, 4:8, 4:9, 4:10, 3:1, 3:2, 3:3, 3:4, 3:5, 3:6, 3:7, 3:8, 3:9, 3:10, 2:1, 2:2, 2:3, 2:4, 2:5, 2:6, 2:7, 2:8, 2:9, 2:10 1:1, 1:2, 1:3, 1:4, 1:5, 1:6, 1:7, 1:8, 1:9, 1:10. These values can define a range, such as about 2:1 to about 1:2, or about 10:2 to about 2:10, or about 8:3 to about 3:8. In some embodiments, the ratio is 1:1.

The bird repellent blend can be applied to surfaces in any way that is effective in preventing or reducing bird damage. The present disclosure relates to a method of reducing or preventing bird damage to a substrate, the method including applying to a surface of the substrate the bird repellent blend of the present disclosure.

In one embodiment, the bird repellent blend of the present disclosure can be applied to the substrate in the form of a solution. The solution can be an aqueous or semi-aqueous solution. The solution can be applied to the substrate using known techniques, such as coating, spraying, dipping, soaking, and knifing and pressure treatment.

The concentration of bird repellent blend that can be applied to the exterior substrate surfaces can be about 0.01, 0.05, 0.1, 0.2, 0.3, 0.4, 0.5, 0.6, 0.7, 0.8, 0.9, 1, 5 or about 10 oz per sq.ft. These values can define a range, such as about 0.3 to about 0.5 oz per sq.ft. The concentration of bird repellent applied to the exterior substrate surface can be about 0.0025, 0.01, 0.03, 0.05, 0.07, 0.09, 0.1, 0.2, 0.3, 0.4, 0.5, 0.6, 0.7, 0.8, 0.9, 1 or about 5 oz per sq.ft. These values can define a range, such as about 0.05 to about 0.2 oz per sq.ft., or about 0.01 to about 10 oz per sq.ft.

It was found that when the bird repellent blend is applied to the substrate surface, the bird repellent composition exhibited improved retention on, or in, the substrate surface as compared to the bird repellent composition alone or in another composition. The bird repellent composition was retained at about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 70%, 60% or about 50% of the concentration as originally applied over time. These values can define a range, such as about 99% to about 95%. The bird repellent composition can be retained at these high levels up to about 5 days, 10, 20, 30, 40, 50, 60, 70, 80, 90, 120, 150, 180 or about 360 days. These values can define a range, such as about 60 to about 120 days. For example, the bird repellent composition can be retained at about 90-99% for up to about 120 days. The bird repellent composition retention when applied to a substrate surface exposed to normal, external weather conditions can be improved by about 20%, 30%, 40%, 50%, 60%, 70%, 80%, 90%, 100%, 200%, 300%, 400% or about 500% compared to the bird repellent composition retention when applied alone or in another composition.

Bird Repellent Compositions

The bird repellent composition of the present disclosure incorporated onto exterior substrate surfaces, or into building materials can be selected from any known effective bird repellent compound, including the quinone compounds provided below. Some examples of other bird repellent compositions include, but are not limited to, methyl anthranilate, dimethyl anthranilate, terpenes such as limonene and d-pulegone, as well as compounds of the formulas:

$$R_1-(S)_x-R_1 \qquad (I)$$

$$R_2-S-R_2 \qquad (II)$$

wherein each $R_1$ is an alkyl radical containing from 1 to 12 carbon atoms, inclusive, x is an integer of from 2 to 8, inclusive, and each $R_2$ is selected from the group consisting of aryl, alkaryl, and aralkyl radicals containing from 6 to 12 carbon atoms, inclusive, are excellent repellents for birds.

Some examples of compounds covered by the above formulas include:
Di-n-butyl pentasulfide
Dimethyl trisulfide
Di-n-propyl tetrasulfide
Di-tert-butyl hexasulfide
Di-sec-octyl heptasulfide
Diethyl octasulfide
n-Propyl n-butyl pentasulfide
Di-n-decyl tetrasulfide
Di-tert-dodecyl hexasulfide
Diphenyl sulfide
Dibenzyl sulfide
Di-p-tolyl sulfide
Di(4-phenylhexyl) sulfide
DJnaphthyl sulfide
Di(2-ethylnaphthyl) sulfide
Di(4-n-hexylphenyl) sulfide
Polycyclic Quinones Composition A wide variety of polycyclic quinones can be used as the bird repellent composition in the invention. As used herein, the term "polycyclic quinone" refers to bicyclic, triciclid and tetracyclic condensed ring quinones and hydroquinones, as well as precursors thereof. On the whole, the non-ionic polycyclic quinones and polycyclic hydroquinones (herein referred to collectively as PCQs) have very low solubility in water at ambient temperatures. For use in the invention, it is preferred that such PCQs have a water solubility no higher than about 1,000 ppm, by weight.

A distinct advantage of the PCQ compounds that have been tested for use in the invention is that they are essentially non toxic, i.e., they have an $LD_{50}$ of at least 2,000 mg/kg in rats and preferably an $LD_{50}$ in rats of 5,000 mg/kg or higher. Because of this low toxicity of PCQs, they are not toxic to most insects or to birds, animals and humans. Moreover, the toxicity level is sufficiently low that any active material that becomes leached into the soil will not be detrimental to the normal constituents of fertile soil layers.

It is important to note that the source of the PCQ used for bird repellency is an important criteria to ensure low toxicity. For example, applicants have registered with the U.S. EPA the PCQ known as 9,10-anthraquinone as a safe, non-toxic PCQ for use as a bird repellent (see U.S. EPA Pesticide Fact Sheet for Anthraquinone, December 1998). It is within the scope of those having ordinary skill in the art to substitute other non-toxic PCQ's in place of anthraquinone for use in the present invention.

However, as noted above, certain precursors of such PCQs can also be used in the invention, either combined with the relatively insoluble PCQs or by themselves. Such precursors are anionic salts of PCQs which are water soluble under alkaline anaerobic conditions. However, these materials are not stable and are easily converted to the insoluble quinone form upon exposure to air. Thus, when anionic PCQs are applied to plants and exposed to air, they are quickly changed to the water-insoluble, more active quinone form.

Among the water-insoluble PCQs that can be used as bird repellent compositions in the invention are anthraquinone, 1,2-dihydroxy anthraquinone, 1,4-dihydroxy anthraquinone, naphthoquinone, anthrone(9,10-dihydro-9-oxo-anthracene), 10-methylene-anthrone, phenanthrenequinone and the alkyl, alkoxy and amino derivatives of such quinones, 6,11-dioxo-1H-anthra[1,2-c]pyrazole, anthraquinone-1,2-naphthacridone, 7,12-dioxo-7,12-dihydroanthra[1,2-b]pyrazine, 1,2-benzanthraquinone, 2,7-dimethylanthraquinone, 2-methylanthraquinone, 3-methylanthraquinone, 1-aminoanthraquinone and 1-methoxyanthraquinone. In addition, more complex polycyclic quinone compounds can be used, such as 2-carboxy-1,3,5,6,8-pentahydroxy-7-monosaccharide and other saccharides of anthraquinones or glucosamides and 2(1,3-dihydro-3-oxy-5-sulfo-2H-indol-2-ylidine)-2,3-dihydro-3-oxo-1H-indole-5-sulfonic acid, disodium salt. Of the foregoing cyclic ketones, anthraquinone and 1,4-dihydroxyanthraquinone are preferred because they appear to be more effective. Naturally occurring anthraquinones can be used as well as synthetic anthraquinones.

Other PCQs which can be used include insoluble anthraquinone compounds, such as 1,8-dihydroxy-anthraquinone, 1-amino-anthraquinone, 1-chloro-anthraquinone, 2-chloro-anthraquinone, 2-chloro-3-carboxyl-anthraquinone and 1-hydroxy-anthraquinone. Various ionic derivatives of these materials can be prepared by catalytic reduction in aqueous alkali.

In addition, a wide variety of anthrahydroquinone compounds can serve as the bird repellent composition in the method of the invention. As used herein, the term "anthrahydroquinone compound" refers to compounds comprising the basic tricyclic structure such as 9,10-dihydroanthrahydroquinone, 1,4-dihydroanthrahydroquinone, and 1,4,4a,9a-tetrahydroanthrahydroquinone. Anthrahydroquinone itself is 9,10-dihydroxyanthracene.

More particularly, both water-insoluble and water-soluble forms can be used. The non-ionic compounds are largely insoluble in aqueous systems, while ionic derivatives, such as di-alkali metal salts, are largely soluble in water. The water soluble forms are stable only in high pH anaerobic fluids. Low pH fluids (pH less than about 9-10) will result in the formation of the insoluble molecular anthrahydroquinone. Aerobic solutions will incur oxidation of the anthraquinones to anthraquinone. Thus, anthrahydroquinones will not exist for long periods of time in an aerated environment, such as that which is experienced by spraying. For these reasons, anthrahydroquinone treatments are usually implemented with the soluble ionic form in a caustic solution. Sodium hydroxide solutions are preferred over the hydroxides of other alkali metals for economic reasons.

Configuration

The PCQ used should be in physical form small enough to be touched by the sensory organs of the bird. Thus, for the PCQ to be more effective as a repellent, it is preferred to be of sufficiently small particle size that its presence can be sensed. Thus, the more effective quantity of repellent in any application is that which is in a form accessible to the birds' nerve endings; that is, it should be of sufficiently small size that it can be orally sensed.

Generally, because of these criteria, particles larger than about 50 micrometers cannot be adequately sensed and particles no larger than 30 micrometers are preferred. Similarly, smooth continuous surfaces of PCQ cannot be adequately sensed; and, of course, if the PCQ is coated with anything which is non-repellent to the bird or to which the bird is taste insensitive, the PCQ is ineffective. Though, strictly speaking, for the PCQ to be effective as a repellent it does not have to be in the form of discrete particles; nevertheless, the particles must be of sufficient size or have a contour that contains areas that are taste-accessible.

When the PCQ is applied directly in particulate form, the size of the particles can be readily controlled. When such particles are applied as a single layer of particles, substantially all of the PCQ would be effective. However, if the particles are applied as a multiple of particle layers, essentially only the top layer would be effective. An important aspect of this analysis is that it is not important that the PCQ be applied as continuous covering. To the contrary, in certain embodiments it may be better that the coating of PCQ particles be discontinuous, at least on a micro scale. Thus, the particles to be effective must be "particulated" in the sense that they contain areas which are accessible to the avian taste nerve endings.

It is the inventor's determination that it is preferred that the concentration of polycyclic quinone to be applied to the surface can be about 0.0025, 0.01, 0.03, 0.05, 0.07, 0.09, 0.1, 0.2, 0.3, 0.4, 0.5, 0.6, 0.7, 0.8, 0.9, 1 or about 5 oz per sq.ft. These values can define a range, such as about 0.05 to about 0.2 oz per sq.ft.

Coadjuvants

As used herein, the term "coadjuvant" refers to materials which have a bio-activity different than the bird repellents themselves. Such materials include contact repellents, fungicides, pesticides, and mixtures thereof. Both liquid and solid coadjuvants can be used in conjunction with the bird repellents of the invention, depending on the manner of application. (See discussion below.) It should be noted, however, that the use of fungicides and pesticides as adjuvants may not be preferred because of the poisonous nature of such adjuvants.

An important class of coadjuvant for use in combination with the bird repellents are trigeminal repellents, i.e., repellents which repel birds when the bird tastes the material. It has been found that terpene-based compounds are particularly useful for this purpose. Limonene, pinene and pulegone are terpenes which are preferred for this purpose. However, polymeric terpenes are also useful for this purpose, especially low molecular weight polymeric terpenes, which are sticky in character.

When terpenes are used as co-repellents with the bird repellents, they will ordinarily constitute a major part of the composition and the bird repellents will constitute only a minor part. For example, composition comprising as little as 1% wt. bird repellent in terpene (including polymeric terpenes) can be used effectively. Though still higher bird repellent concentrations can be used, it will not be necessary to use more than about 10% wt. On the other hand, as little as 10% wt. terpene compound can be used, at least 30% being preferred to enhance the contact repellency properties.

Other trigeminal repellents, such as pepper and 2-hydroxyacetophenone, and methylanthranalate, can also be used in admixture with the bird repellent and admixtures of the bird repellent with other trigeminal repellents.

Additives

As used herein, the term "additives" refers to materials which augment the effectiveness of the compositions of the invention, but which do not by themselves have bio-activity. These include such materials as surfactants, wetting agents, defoaming agents, extenders, sticking agents, penetrants, plasticizers, activators, spreading agents, diluents, odorants and the like.

It will be recognized from the foregoing discussion that not all of the bird repellent coatings may be of suitable configuration. However, so long as a sufficient fraction of the coating is available to the birds' nerve endings, the composition will effectively deter them from the surface. As mentioned above, access of the bird repellent to the nerve receptor sites of the bird may occur during pecking of the treated surfaces.

It will be recognized that other dispersion media than water can be used. For example, safe, degradable oils, such as vegetable oils, can be used. However, from the standpoint of safety and environmental health, it is much preferred to use water.

Other additives that may be used in formulating an effective bird repellent blend of the current invention include pigments, film-forming aids, coalescing agents, additives for properties such as regulating flow and leveling, sheen, foaming, yellowing, resistance to stains and for retaining color. Additional additives may include coalescing agents, dispersing agents, anti-blistering agents, surfactants, rheology modifiers, defoamers, thickeners, biocides, anti-fungals, anti-mildew agents, colorants, waxes, perfumes and co-solvents, surface-active dispersing or wetting agents, and functional extenders.

The disclosures of all cited references including publications, patents, and patent applications are expressly incorporated herein by reference in their entirety. When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

Initial testing of Arkion's Flight Control anthraquinone (AQ) based bird repellent surface coating was unsuccessful:

AQ Treatment Study:

Poles: (2) Creosote treated Southern Yellow Pine poles, 8" diameter×36" section (2) Pentachlorophenol treated Western Red Cedar poles, 11" diameter×36" section Prior to treating the poles, the AQ formulation container was placed on a paint mixing device for approximately 5 minutes. A total of 50 oz of Flight Control product was applied by paint roller to 3 ft sections of 4 poles. Temperature was 66° F. following treatment for at least 2 hours. Total AQ application: 50 oz or 1.6 oz per sq ft, equivalent to 0.8 oz AQ per sq. ft. The appearance of the treated zones resembled a latex paint application.

Figure 2:
FIG. 2 is a photographic image of the pole from FIG. 1 eight (8) days post application.
Figure 3:
FIG. 3 is a photographic image of the pole from FIG. 1 twenty one (21) days post application.

Between Oct. 31, 2015 and Nov. 20, 2015 there was approximately 1.5 inches of precipitation and temperatures ranged from 20° F. to 66° F. Attached are photos of the application on treatment day (FIG. 1), 8 days post treatment (FIG. 2) and 21 days post treatment (FIG. 3). By visual assessment, the coatings were substantially damaged during the test period.

Example 2

The AQ product from Example 1 was reformulated to improve weatherability.

Example Formulations

1. Equal volume mix of AQ formulation and Kilz® Premium
2. Equal volume mix of AQ formulation and Kilz® Complete
3. Equal volume mix of AQ formulation and Kilz® Clear All three formulations were applied by roller at a 300 square foot/gallon coverage rate, equivalent to 0.4 oz per sq.ft, equivalent to 0.1 oz AQ/sq. ft. All three formulations were tested on sections of outdoor creosote utility poles, and in all cases the addition of AQ to the Kilz® Primer turned the final product a light whitish tan color which remained that color on the pole. By visual assessment, all products have remained intact under rain, freezing rain, snow and hot/cold temperatures ranging from 65° F. to −5° F.

Figure 4:
FIG. 4 is a photographic image of a pole treated with a blend of anthraquinone and a 1st paint coating composition on the day of application.
Figure 5:
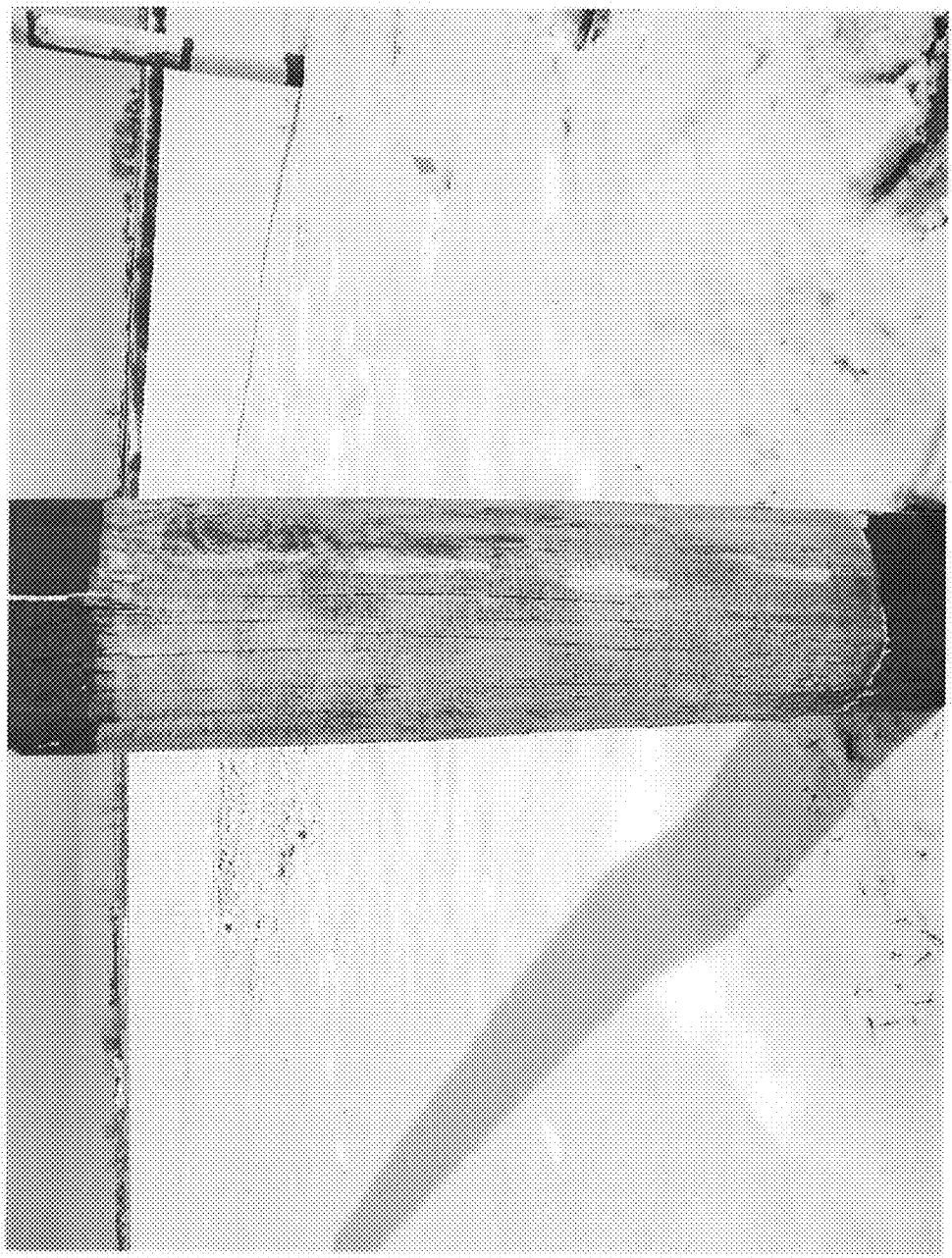
FIG. 5 is a photographic image of the pole from FIG. 4 fifty three (53) days post application.
Figure 6:
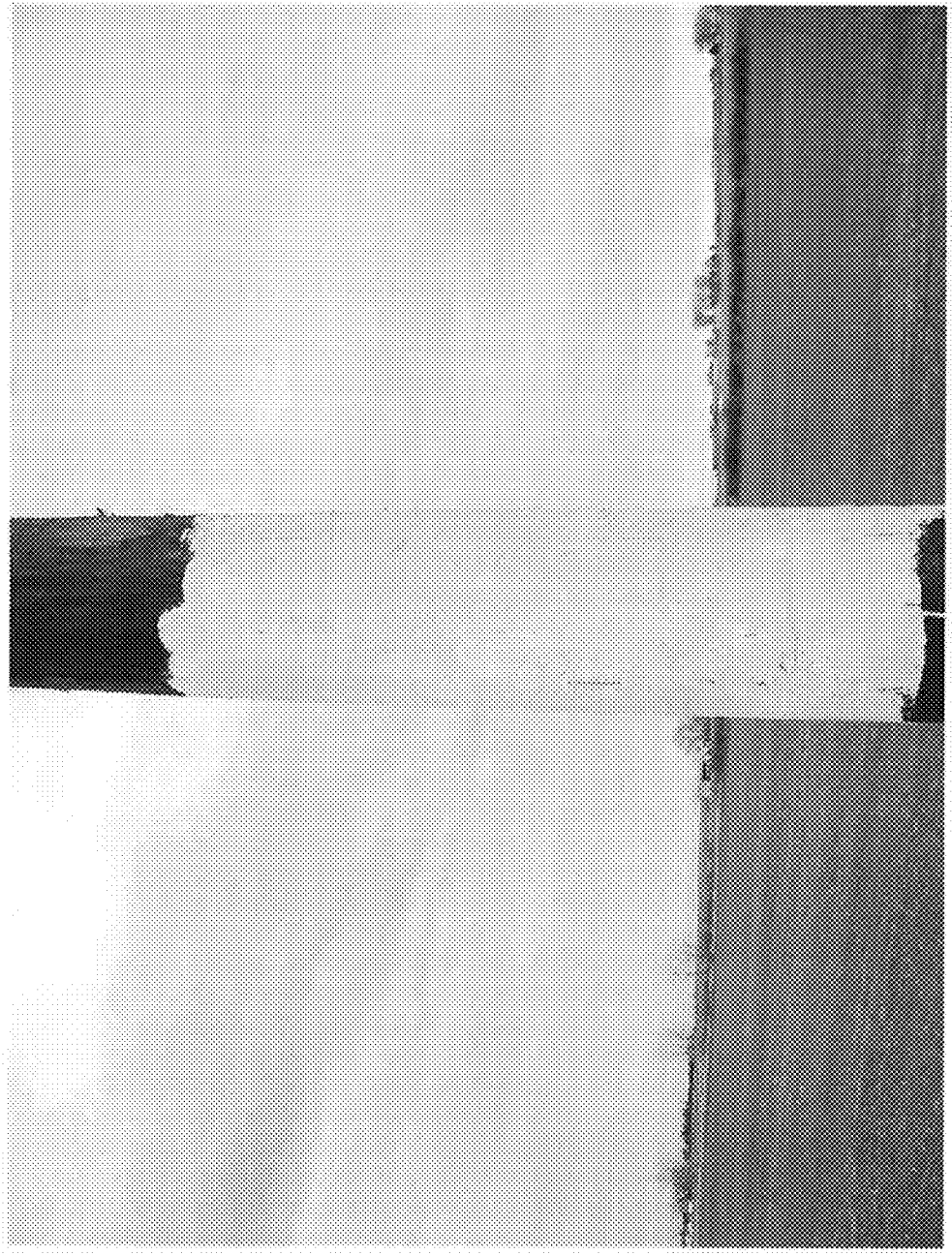
FIG. 6 is a photographic image of a pole treated with a blend of anthraquinone and a 2nd paint coating composition on the day of application.
Figure 7:
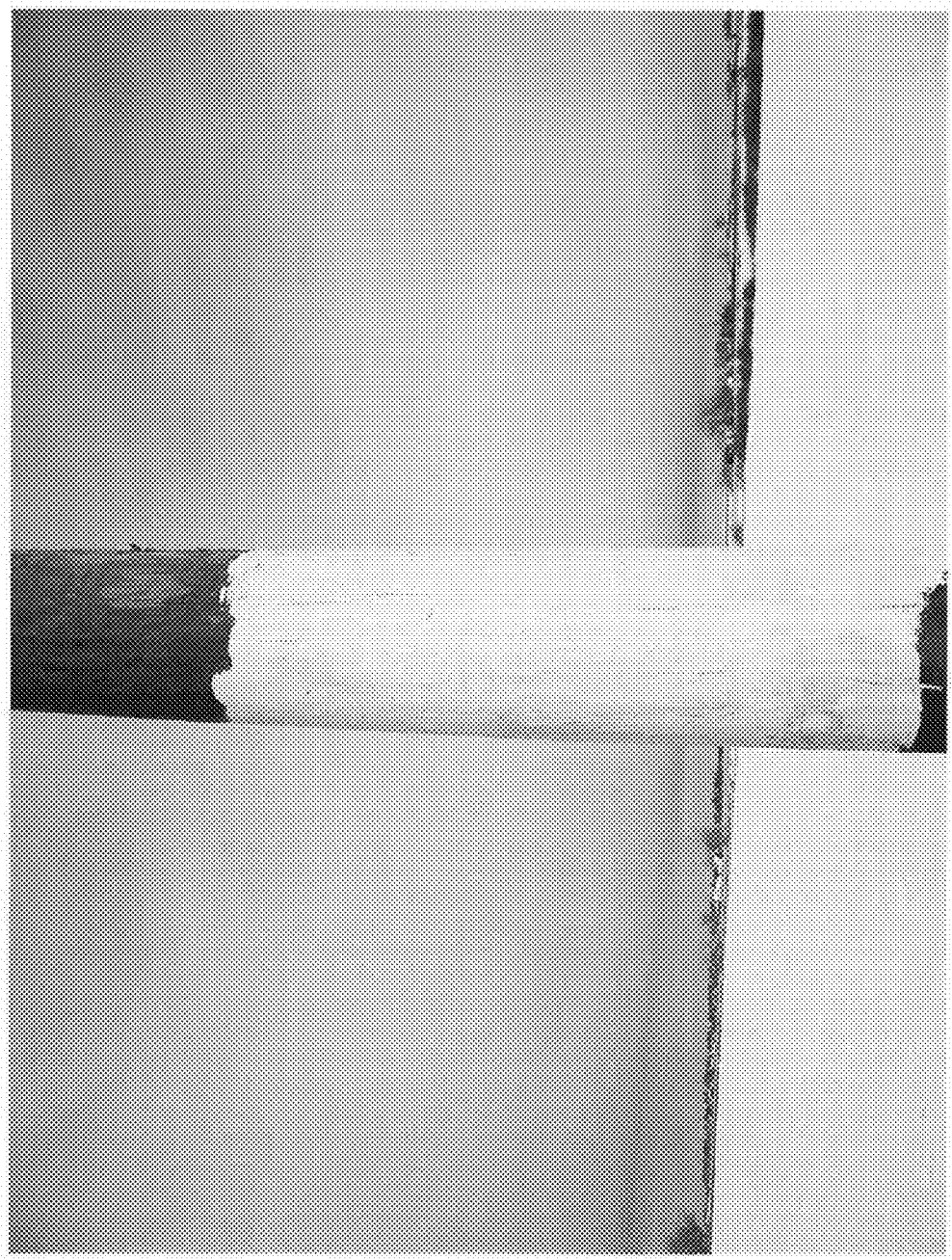
FIG. 7 is a photographic image of the pole from FIG. 6 fifty three (53) days post application.
Figure 8:
FIG. 8 is a photographic image of a pole treated with a blend of anthraquinone and a 3rd paint coating composition on the day of application.
Figure 9:
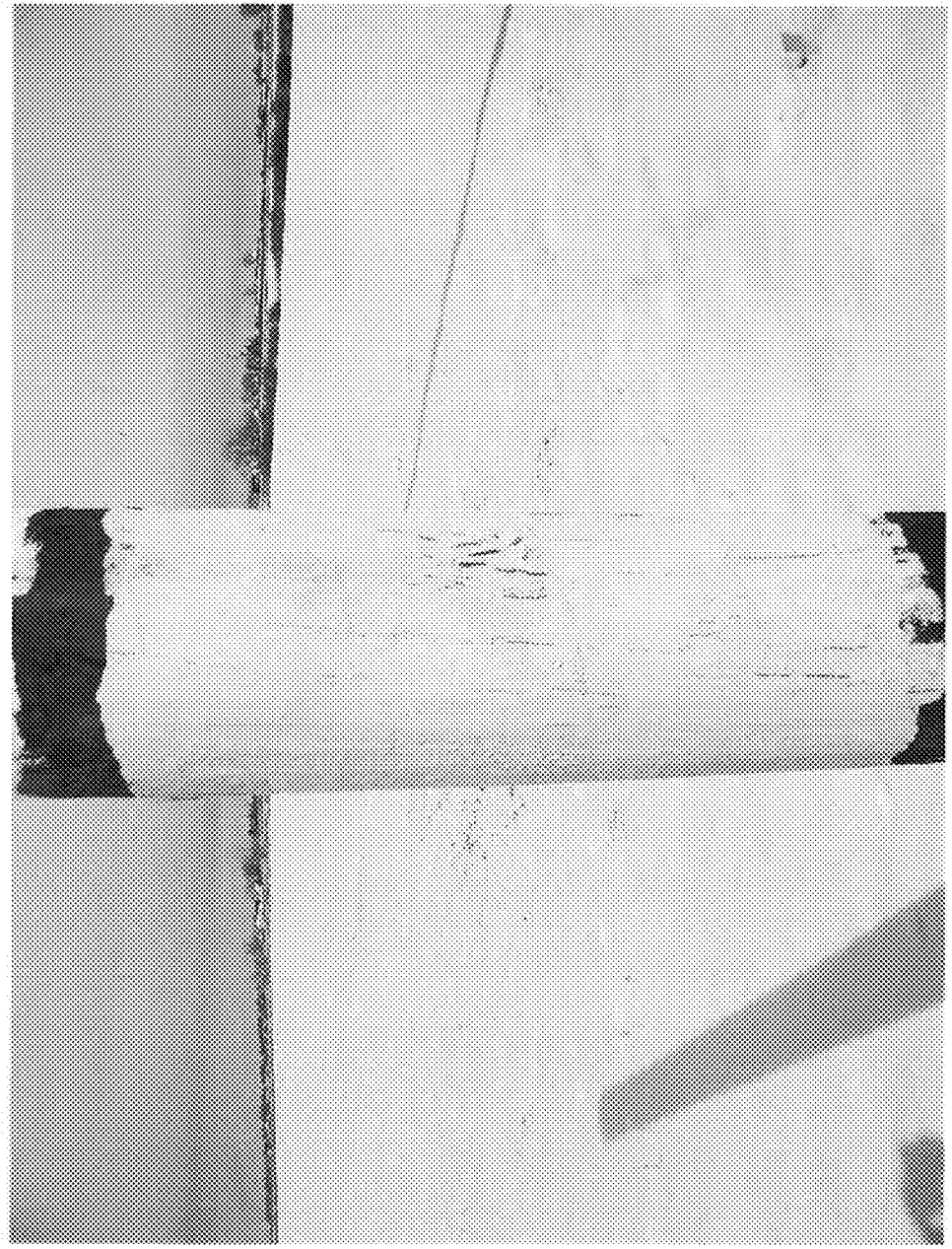
FIG. 9 is a photographic image of the pole from FIG. 8 fifty three (53) days post application.

Attached are photos of the application on treatment day (FIG. 4 AQ+Kilz® Premium; FIG. 6 AQ+Kilz® Complete; FIG. 8 AQ+Kilz® Clear) and 53 days post treatment (FIG. 5 AQ+Kilz® Premium; FIG. 7 AQ+Kilz® Complete; FIG. 9 AQ+Kilz® Clear).

Kilz® Premium:

| Chemical Name | CAS# | Ingredient Percent |
|---|---|---|
| Limestone | 1317-65-3 | 5-10 by weight |
| Nepheline Syenite | 37244-96-5 | 5-10 by weight |
| Titanium dioxide | 3463-67-7 | 10-30 by weight |

Kilz® Complete:

| Chemical Name | CAS# | Ingredient Percent |
|---|---|---|
| Silicate, mica | 12001-26-2 | 10-30 by weight |
| Calcium carbonate (limestone) | 1317-65-3 | 5-10 by weight |
| Titanium dioxide | 13463-67-7 | 5-10 by weight |
| Distillates (petroleum), hydrotreated light; Kerosine-unspecified | 64742-47-8 | 10-30 by weight |
| Nepheline Syenite | 37244-96-5 | 1-5 by weight |
| Amorphous Silica | 112926-00-8 | 1-5 by weight |
| Rutile | 1317-80-2 | 5-10 by weight |
| Aliphatic Hydrocarbon | 64742-49-0 | 5-10 by weight |
| Mineral spirits | 8052-41-3 | 1-5 by weight |

Kilz® Clear:

| Chemical Name | CAS# | Ingredient Percent |
|---|---|---|
| Ethylene glycol | 107-21-1 | 1-5 by weight |
| Silica, amorphous-diatomaceous earth | 61790-53-2 | 1-5 by weight |

Example 3

Samples of the extended performance bird repellent coatings from Example 2 were analyzed by the United States Department of Agriculture Animal Plant Health Inspection Service Wildlife Services National Wildlife Research Center Chemistry Lab Unit to determine AQ retention over time. The results show that all three formulations maintained AQ concentrations at the levels they were applied over the course of 113 days of weather exposure. The protocols and results follow:

Sample Description:

Three Kilz® brand paint formulations, one Airepel® formulation and seven bags of wood chips with applied paint formulations collected from power poles were received in March, 2016 for anthraquinone analysis. The samples were stored refrigerated until time of analysis. Sample descriptions can be found on pages 2-3 of this report.

Method Information:

Kilz® paint/Airepel® formulations:

A 0.150 mL sample of thoroughly mixed paint formulation was dispensed into a 50-mL disposable polypropylene tube and the mass recorded to ±0.1 mg. Three ml of deionized water was added to disperse the formulation, followed by 30 mL chloroform. The sample was mechanically shaken for 10 minutes and then centrifuged briefly to separate the phases. A portion of the lower chloroform layer was then diluted into a microcentrifuge tube and clarified at 16,000 RCF prior to GC analysis.

Power Pole Wood Chips with Applied Kilz® Paint Formulations:

Wood chip samples were ground into a fine powder using a blender and dried at 60° C. for 16 hours. A 1.5 g sample was weighed into a 50-mL disposable polypropylene tube and extracted on a mechanical shaker with 20 mL chloroform. The sample was then vacuum filtered through a Whatman 40 filter. A portion of the filtrate was then diluted into a microcentrifuge tube and clarified at 16,000 RCF prior to gas chromatographic analysis. The remaining wood chips were then dried for 4 hours at 60° C. The mass of the wood chips was subtracted from the initial sample weight to determine the amount of paint formulation in the sample.

Instrumental Method:

Standards and samples were diluted in 2:1 chloroform:hexanes. Anthraquinone was quantitated using an Agilent 7890A gas chromatograph (GC) with flame ionization detector (FID).

| Column: | HP-5MS UI, 0.25 µm × 0.25 mm × 15 m |
|---|---|
| Carrier gas: | $H_2$, 3.5 mL/min (constant flow) |
| Inlet: | 990 µL straight liner, 300° C., split 8:1 |
| Injection volume: | 1 µL |
| Run time: | 7.25 min. (including 2.0 min. post time) |

| Time (min) | T (° C.) | Rate (° C./min) | Hold (min.) |
|---|---|---|---|
| 0.00 | 130 | — | 0.50 |
| 4.75 | 225 | 20 | 0.00 |

| Detector: | FID |
|---|---|
| Heater: | 300° C. |
| H2 flow: | 50 mL/min. |
| Air flow: | 400 mL/min. |
| Makeup flow: | 25 mL/min. |

A six-level standard curve ranging from 5.7 to 326 µg/ml, anthraquinone was used. The standard curve below 37 µg/mL, became non-linear, but all samples containing anthraquinone were above this concentration.

Results:

The observed anthraquinone concentrations presented in Tables 1 and 2 are expressed as the percentage of anthraquinone weight divided by the weight of formulation (% w/w).

TABLE 1

Anthraquinone (AQ) content (% w/w) in Kilz ® paint and Airepel ® formulations.

| Sample ID | Sample Description | Observed AQConc. (% w/w) | | |
|---|---|---|---|---|
| Sample 001-A | | 25.5% | $Ave_{(n-3)}$ = | 25.4% |
| Sample 001-B | Kilz ® Complete (25% AQ) | 25.6% | Std dev = | 0.21% |
| Sample 001-C | | 25.2% | CV = | 0.83% |
| Sample 002-A | | 23.7% | $Ave_{(n-3)}$ = | 23.8% |
| Sample 002-B | Kilz ® Premium (25% AQ) | 23.8% | Std dev = | 0.058% |
| Sample 002-C | | 23.8% | CV = | 0.24% |
| Sample 003-A | | 23.1% | $Ave_{(n-3)}$ = | 23.3% |
| Sample 003-B | Kilz ® Clear (25% AQ) | 23.1% | Std dev = | 0.35% |

TABLE 1-continued

Anthraquinone (AQ) content (% w/w) in Kilz ® paint and Airepel ® formulations.

| Sample ID | Sample Description | Observed AQConc. (% w/w) | | |
|---|---|---|---|---|
| Sample 003-C | | 23.7% | CV = | 1.5% |
| Sample 004-A | | 49.6% | Ave$_{(n=3)}$ = | 50.6% |
| Sample 004-B | Airepel ® (50% AQ) | 51.0% | Std dev = | 0.91% |
| Sample 004-C | | 51.3% | CV = | 1.8% |

Detection Limit = 0.14% AQ (w/w)

TABLE 2

Anthraquinone (AQ) content (% w/w) in Kilz ® paint formulations applied to wooden power poles

| Sample ID | Sample Description | Observed AQConc. (% w/w) | | |
|---|---|---|---|---|
| Sample 005-A | Creosote only | ND | | |
| Sample 005-B | | ND | | |
| Sample 006-A | Kilz ® Complete only | ND | | |
| Sample 006-B | | ND | | |
| Sample 007-A | Kilz ® Complete (25% AQ) | 29.3% | Ave$_{(n=2)}$ = | 23.3% |
| Sample 007-B | | 27.9% | Std dev = | 0.35% |
| | | | CV = | 3.5% |
| Sample 008-A | Kilz ® Premium only | ND | | |
| Sample 008-B | | ND | | |
| Sample 009-A | Kilz ® Premium (25% AQ) | 21.9% | Ave$_{(n=2)}$ = | 22.2% |
| Sample 009-B | | 22.4% | Std dev = | 0.35% |
| | | | CV = | 1.6% |
| Sample 010-A | Kilz ® Clear only | ND | | |
| Sample 010-B | | ND | | |
| Sample 011-A | Kilz ® Clear (25% AQ) | 20.2% | Ave$_{(n=2)}$ = | 22.7% |
| Sample 011-B | | 25.3% | Std dev = | 3.6% |
| | | | CV = | 16% |

ND = Not Detected
Detection Limit = 0.14% AQ (w/w)

We claim:

1. A bird repellent coating blend comprising a bird repellent composition and a paint coating composition, wherein the bird repellent composition is anthraquinone, and wherein the bird repellent composition comprises from about 10 wt % to about 60 wt % of the bird repellent coating blend.

2. The bird repellent coating blend of claim 1 wherein the paint coating composition is selected from the group consisting of acrylic polymers, acrylic primers, acrylic paints, acrylic/latex primers, acrylic/latex paints, alkyd-based primers, alkyd-based paints, hydrophobic polymers, water-based acrylic emulsion primers, water-based acrylic emulsion paints, acrylic sealing primers, acrylic sealing paints, styrene acrylic primer, styrene acrylic paint, polyurethane latex primers, polyurethane latex paints, and any combinations thereof.

3. The bird repellent coating blend of claim 1 wherein the volume ratio of the bird repellent composition to the paint coating composition is from about 10:1 to about 1:10.

4. The bird repellent coating blend of claim 1 wherein the bird repellent composition has a melting temperature of at least about 100° C.

5. The bird repellent coating blend of claim 1 wherein the bird repellent composition has a solubility in pure water under ambient temperature conditions of from about 0.01 ppm to about 200 ppm.

6. An exterior substrate comprising a bird repellent coating blend wherein the bird repellent coating blend comprises a bird repellent composition and a paint coating composition, wherein the bird repellent composition is anthraquinone,
and wherein the bird repellent composition comprises from about 10 wt % to about 60 wt % of the bird repellent coating blend.

7. The exterior substrate of claim 6 wherein the exterior substrate is selected from the group consisting of wood, creosote treated wood, non-creosite treated wood, power poles, telephone poles, outdoor lumber, dimensional lumber, pressure treated lumber, shingles, siding, decking surfaces, porch surfaces, plastics, architectural foam, stucco, and artificial wood products.

8. The exterior substrate of claim 6 wherein the paint coating composition is selected from the group consisting of acrylic polymers, acrylic primers, acrylic paints, acrylic/latex primers, acrylic/latex paints, alkyd-based primers, alkyd-based paints, hydrophobic polymers, water-based acrylic emulsion primers, water-based acrylic emulsion paints, acrylic sealing primers, acrylic sealing paints, styrene acrylic primer, styrene acrylic paint, polyurethane latex primers, polyurethane latex paints, and any combinations thereof.

9. The exterior substrate of claim 6 wherein the volume ratio of the bird repellent composition to the paint coating composition is from about 10:1 to about 1:10.

10. The exterior substrate of claim 6 wherein the bird repellent composition has a melting temperature of at least about 100° C.

11. The exterior substrate of claim 6 wherein the bird repellent composition has a solubility in pure water under ambient temperature conditions of from about 0.01 ppm to about 200 ppm.

12. A method of applying a bird repellent composition to an exterior substrate, the method comprising:
preparing a bird repellant blend according to claim 1 comprising a bird repellent composition and a paint coating composition;
adhering said bird repellent blend to said exterior substrate;
whereby said bird repellent composition remains adhered to said exterior substrate for a period of time longer than when said bird repellent composition is applied to said substrate without being blended with the paint coating composition; and whereby the bird repellent composition remains bioavailable during the period of time that the bird repellent blend is adhered to the exterior surface.

* * * * *